(12) United States Patent
Dong et al.

(10) Patent No.: US 12,678,221 B2
(45) Date of Patent: Jul. 14, 2026

(54) CORRUGATED RADIOFREQUENCY ABLATION CATHETER HAVING WALL-ATTACHING ADJUSTMENT WIRE AND APPARATUS THEREOF

(71) Applicant: Shanghai Golden Leaf Med Tec Co., Ltd., Shanghai (CN)

(72) Inventors: Yonghua Dong, Shanghai (CN); Meijun Shen, Shanghai (CN)

(73) Assignee: Shanghai Golden Leaf Med Tec Co., Ltd., Shanghai (CN)

( * ) Notice: Subject to any disclaimer, the term of this patent is extended or adjusted under 35 U.S.C. 154(b) by 798 days.

(21) Appl. No.: 18/089,753

(22) Filed: Dec. 28, 2022

(65) Prior Publication Data

US 2023/0129393 A1 Apr. 27, 2023

Related U.S. Application Data

(63) Continuation-in-part of application No. 15/573,462, filed as application No. PCT/CN2016/081621 on May 10, 2016, now abandoned.

(30) Foreign Application Priority Data

| | | | |
|---|---|---|---|
| May 13, 2015 | (CN) | .......................... | 201510244254.2 |
| Aug. 12, 2015 | (CN) | .......................... | 201510492572.0 |
| Aug. 12, 2015 | (CN) | .......................... | 201520605029.2 |

(51) Int. Cl.
*A61B 18/14* (2006.01)
*A61B 18/00* (2006.01)

(52) U.S. Cl.
CPC ..... *A61B 18/1492* (2013.01); *A61B 2018/00273* (2013.01); *A61B 2018/00577* (2013.01); *A61B 2018/144* (2013.01)

(58) Field of Classification Search
CPC ...... A61B 18/1492; A61B 2018/00273; A61B 2018/00577; A61B 2018/144
See application file for complete search history.

(56) References Cited

U.S. PATENT DOCUMENTS

| | | | | | |
|---|---|---|---|---|---|
| 5,687,723 | A | | 11/1997 | Avitall | |
| 5,921,924 | A | * | 7/1999 | Avitall | ................. A61B 5/6855 |
| | | | | | 600/374 |

(Continued)

FOREIGN PATENT DOCUMENTS

| | | |
|---|---|---|
| CN | 101309651 | 11/2008 |
| CN | 102488552 | 6/2012 |

(Continued)

*Primary Examiner* — Ronald Hupczey, Jr.

(57) ABSTRACT

A corrugated radiofrequency ablation catheter having wall-attaching adjustment wires (6, 6A, 6B, 6A', and 6B'), provided with a strip-shaped connecting catheter, an electrode frame provided at the front end of the connecting catheter, and a control handle (20) provided at the rear end of the connecting catheter. The electrode frame is a corrugated electrode frame consisting of one or more corrugations, where one or more electrodes (2) respectively are distributed on the corrugations. The rear sections of the wall-attaching adjustment wires (6, 6A, 6B, 6A', and 6B') are slidably provided within one lumen of the connecting catheter and are connected at the rear extremities (60) onto a control element (22) provided on the control handle (20) or connected onto a control element (22) provided outside of the control handle (20).

14 Claims, 12 Drawing Sheets

(56)                    References Cited

U.S. PATENT DOCUMENTS

| | | | |
|---|---|---|---|
| 6,542,781 | B1 | 4/2003 | Koblish et al. |
| 9,561,121 | B2 | 2/2017 | Sudin et al. |
| 2001/0020174 | A1 | 9/2001 | Koblish |
| 2017/0027640 | A1 | 2/2017 | Kunis et al. |

FOREIGN PATENT DOCUMENTS

| | | |
|---|---|---|
| CN | 104127233 | 11/2014 |
| CN | 203970538 | 12/2014 |
| CN | 105078571 | 11/2015 |
| CN | 205019161 | 2/2016 |
| WO | WO 2014/087245 | 6/2014 |
| WO | WO 2014/166436 | 10/2014 |

* cited by examiner

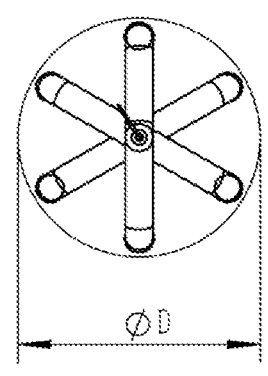
FIG. 7B
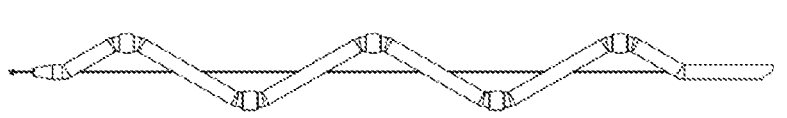 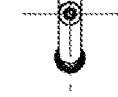
FIG. 8A            FIG. 8B
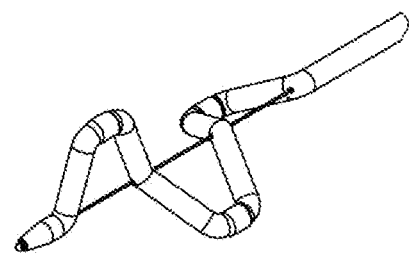 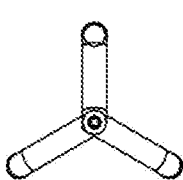
FIG. 9A            FIG. 9B

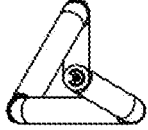
FIG. 10A                    FIG. 10B
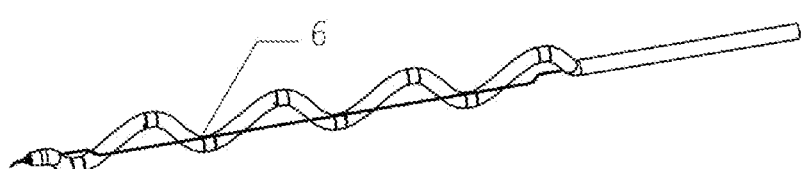
FIG. 11
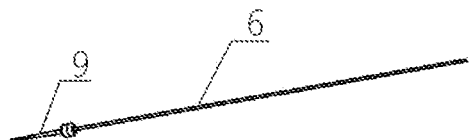
FIG. 12

CORRUGATED RADIOFREQUENCY ABLATION CATHETER HAVING WALL-ATTACHING ADJUSTMENT WIRE AND APPARATUS THEREOF

CROSS-REFERENCE TO RELATED APPLICATIONS

This application is a Continuation-in-Part (CIP) of U.S. patent application Ser. No. 15/573,462 filed on Nov. 11, 2017, which is a National Phase of PCT Patent Application No. PCT/CN2016/081621 having International filing date of May 10, 2016, which claims the benefit of priority of Chinese Patent Application Nos. 201520605029.2 and 201510492572.0, both filed on Aug. 12, 2015, and Chinese Patent Application No. 201510244254.2 filed on May 13, 2015. The contents of the above applications are all incorporated by reference as if fully set forth herein in their entirety.

TECHNICAL FIELD

The present invention relates to a corrugated radiofrequency ablation catheter having a wall-attaching adjustment wire, also relates to a radiofrequency ablation apparatus comprising the radiofrequency ablation catheter, and belongs to the technical field of interventional medical instruments.

RELATED ART

In a radiofrequency ablation system, a radiofrequency ablation catheter is a key device used for human blood vessel intervention and radiofrequency energy release. Radiofrequency electrodes are installed on a frame at the front end of the radiofrequency ablation catheter, the frame is used for bearing the radiofrequency electrodes, and the frame expands to be attached to the wall before radiofrequency starts and retracts after radiofrequency ends. Since radiofrequency ablation surgery is conducted through direct human blood vessel intervention, the expanding and retracting size of the frame needs to be matched with the diameters of human blood vessels.

The diameters of human blood vessels vary with ablation portions. Besides, the diameters of human blood vessels vary from person to person. For example, the renal artery diameters of different persons range from 2 mm to 12 mm, showing a great difference. In the prior art, the expanding and retracting size of the electrode end of the radiofrequency ablation catheter is generally fixed and cannot adapt to different diameters of human blood vessels, thus being small in coverage over human blood vessels with different diameters. Therefore, when radiofrequency ablation surgery is conducted on different patients, radiofrequency ablation catheters of different specifications and models are usually required for ablation. Even so, the problem that radiofrequency electrodes can not be attached to the wall at the same time still exists during certain surgery, and the surgical effect is influenced.

Radiofrequency ablation catheters can be of various structures based on the shape of electrodes and the shape of an electrode frame, such as a balloon type, a puncture needle type, a spiral type and a lobe structure. The adaptability of all existing radiofrequency ablation catheters to blood vessels with different diameters is limited.

SUMMARY

The primary technical problem to be solved by the present invention is to provide a corrugated radiofrequency ablation catheter having a wall-attaching adjustment wire.

Another technical problem to be solved by the present invention is to provide a radiofrequency ablation apparatus comprising the radiofrequency ablation catheter.

In order to achieve the above-mentioned purposes, the present invention adopts the following technical scheme:

according to a first aspect of an embodiment of the present invention, a corrugated radiofrequency ablation catheter having a wall-attaching adjustment wire, provided with a connecting catheter, an electrode frame provided at the front end of the connecting catheter, and a control handle provided at the rear end of the connecting catheter;

the electrode frame is a corrugated electrode frame comprising multiple intermediate sections, each intermediate section having electrodes at both ends thereof;

a rear section of the wall-attaching adjustment wire is slidably provided within the connecting catheter and is connected to the control handle or connected onto a control element provided outside of the control handle; a front section of the wall-attaching adjustment wire protrudes to the outside of the electrode frame and either runs through one or more holes provided on the corrugations or runs around the multiple corrugations, and then the front end returns to the interior of the electrode frame to be fixed.

Preferably, each of the intermediate sections extends along a diameter of a contour circumferential surface, or extends along one side of an inner joint triangle of the contour circumferential surface, the electrodes located on the contour circumferential surface.

Preferably, each of the intermediate sections is of D in length, which is the diameter of the contour circumferential surface.

Preferably, each of the intermediate sections has a through-hole at middle for allowing the wall-attaching adjustment wire to extend into the intermediate sections or extend outwardly from the intermediate sections.

Preferably, the through-hole locates at D/2 of each of the intermediate sections.

Preferably, the electrode frame further comprises a tip section and a rear section, which are of D/2 in length.

Preferably, the wall-attaching adjustment wire penetrate the intermediate sections at pitch of L, D<L<2D, Preferably, the intermediate sections are of D in length.

Preferably, after returning to the interior of the electrode frame, the front end of the wall-attaching adjustment wire runs through lumens in the electrode frame and the connecting catheter, returns to the rear end of the connecting catheter, and is fixed to the control handle or the control element.

Preferably, the corrugated radiofrequency ablation catheter further comprises a supporting wire provided in a certain lumen of the connecting catheter and the electrode frame.

Preferably, the corrugated radiofrequency ablation catheter further comprises a shaping wire provided within the electrode frame.

Preferably, a developing head and/or soft guide wire is provided at the front end of the supporting wire.

Preferably, a second control element used for being fixed to the tail end of the supporting wire is further provided on the control handle or outside the control handle.

Preferably, the wall-attaching adjustment wire is composed of two or more filaments, the multiple filaments are used for adjusting one corrugation or one section of corrugations on the electrode frame respectively, one section of corrugations comprises two or more corrugations, the front end of each filament is fixed to one end of the corresponding corrugation/corrugation section, and the other end of each filament runs around the corresponding corrugation/corrugation section, runs through lumens in the electrode frame and the connecting catheter, and is then fixed to the corresponding control element provided on the control handle or arranged externally.

Preferably, the multiple sections of corrugations controlled by the multiple filaments respectively overlap.

Preferably, the multiple corrugations constituting the electrode frame are provided from the front end to the rear end of the electrode frame in a size increasing mode, or the multiple corrugations constituting the electrode frame are provided from the front end to the rear end of the electrode frame in a size reducing mode.

According to a second aspect of the embodiment of the present invention, a radiofrequency ablation apparatus, comprising the aforesaid radiofrequency ablation catheter and a radiofrequency ablation main unit connected with the radiofrequency ablation catheter.

The radiofrequency ablation apparatus of the present invention provides the following technical advantages: 1) the sizes and construction of the intermediate sections enable the electrodes be pressed firmly and evenly against the wall of the blood vessel along the elongated catheter, which is adapted to ablate elongated blood vessel or the like; 2) multiple electrodes distributed along the elongated catheter and located at both ends of the intermediate section, provides the radiofrequency ablation at one position and then are rotated by the operator to perform the radiofrequency ablation at another position, which improve operation efficiency; 3) the wall-attaching adjustment wire penetrates the intermediate sections at middle of the intermediate sections, thus the intermediate sections could be extended or shorten to adapt to blood vessels with different diameter while provide evenly force against the wall of the blood vessels.

BRIEF DESCRIPTION OF THE DRAWINGS

FIG. 7B is a side view corresponding to FIG. 7A;

FIG. 8A and FIG. 8B are a front view and a side view of a corrugated radiofrequency ablation catheter in a second embodiment respectively;

FIG. 9A and FIG. 9B are a three-dimensional structure diagram and a side view of a corrugated radiofrequency ablation catheter in a third embodiment respectively;

FIG. 10A and FIG. 10B are a three-dimensional structure diagram and a side view of a corrugated radiofrequency ablation catheter in a fourth embodiment respectively;

FIG. 11 is a three-dimensional structure diagram of a corrugated radiofrequency ablation catheter in a fifth embodiment;

FIG. 12 is a first exemplary structure of a wall-attaching adjustment wire in the corrugated radiofrequency ablation catheter shown in FIG. 11;

DETAILED DESCRIPTION

The technical content of the present invention is further described in detail with reference to accompanying drawings and specific embodiments.

First Embodiment

It can be learned from FIG. 1A to FIG. 7B that a corrugated radiofrequency ablation catheter provided by the present invention comprises an elongated connecting catheter 300, a corrugated electrode frame 100 provided at a front end of the connecting catheter 300 (see FIG. 1A), a control handle 20 provided at the rear end of the connecting catheter 300 (see FIG. 5) and a wall-attaching adjustment wire 6. Alternatively, the electrode frame 100 can be manufactured integral with the connecting catheter 300 in one-piece, or, the electrode frame 100 can be independently manufactured and then connected with the connecting catheter 300 as a whole.

Figure 1A:
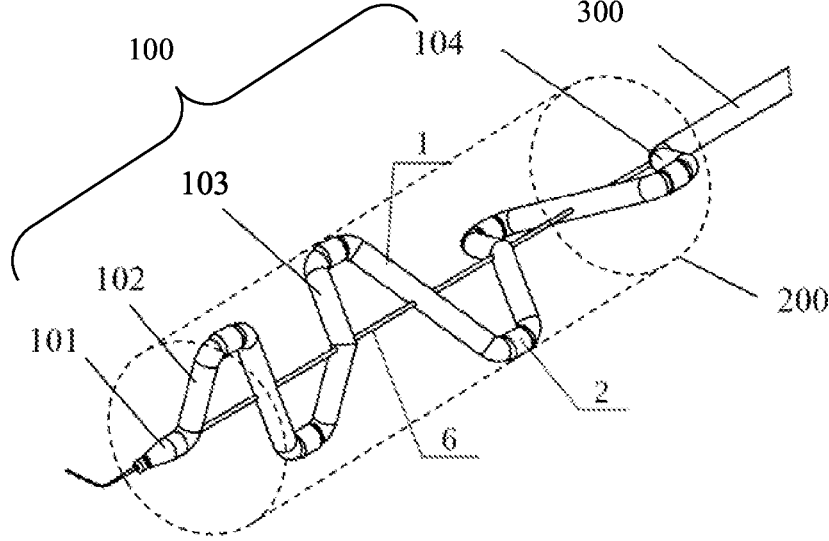
FIG. 1A and FIG. 1B are a three-dimensional structure diagram and a side view of a corrugated radiofrequency ablation catheter in a first embodiment respectively.
Figure 1B:
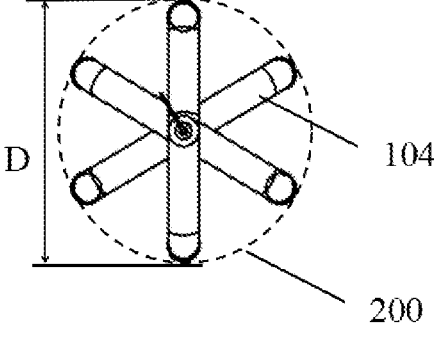

As shown in FIG. 1A and FIG. 1B, the electrode frame 100 is corrugated and comprises an outer tube 1 and multiple electrodes 2 provided on the outer tube 1. The outer tube 1 is preformed to be a corrugated shape consisting of one or more corrugations. Each corrugation can be in the shape of a fold line composed of several straight line segments, such as a triangular wave; each corrugation can also be composed of several curve segments, such as a sine wave or an arc wave; and each corrugation can also be composed of curves and straight lines, such as a trapezoidal wave with a corner. All the electrodes 2 on the electrode frame 100 locate on a contour circumferential surface 200 (as shown in dotted-lines in FIG. 1A). The contour circumferential surface 200, defined by the electrodes 2, extends coaxially with the connecting catheter 300.

The electrode frame 100 comprises same corrugations in same shape and same size, or alternatively comprise corrugations in different shapes and different sizes. Detailed explanation will be provided with reference to specific embodiment. Among the multiple corrugations, some of the corrugations are located in different planes, and others of the corrugations are located in the same plane, which makes the electrode frame 100 extend in three dimensional corrugations within the contour circumferential surface 200.

As are shown in FIGS. 1A and 1B, the outer tube 1 includes a tip section 101, a distal section 102, multiple intermediate sections 103, and a proximal section 104 that are connected in sequence. The connections between the distal section 102, the intermediate section 103, and the proximal section 104 are peripherally covered with electrode material to form electrodes 2. The proximal section 104 is connected to a distal end of the connecting catheter 300.

The distal section 102 and the proximal section 104 are substantially of D/2 in length, where D is the diameter of the contour circumferential surface 200. In addition, length of each intermediate sections 103 is L, D<L<2D. Since the length D is approximately the diameter of a lumen to be ablated by the electrodes 2, the electrode frame 100 is adapted for ablating the lumen with all the electrodes 2 adhering to the wall of the lumen (a blood vessel, for example).

In the first embodiment, every two corrugations are located in the same plane, so that in the side projection plan the multiple corrugations are in a radial shape as shown in FIG. 1B. The multiple electrodes 2 can be distributed on the corrugations respectively, and preferably, the electrodes 2 are provided at the crests or troughs of the corrugations. The electrodes 2 can be block type electrodes or annular electrodes embedded in or surrounded on the outer tube 1. The external surfaces of the electrodes 2 can be flush with the external surface of the outer tube 1 or slightly higher than the external surface of the outer tube 1, and the external surfaces of the electrodes 2 can also be lower than the external surface of the outer tube 1.

It can be learned from the side view as shown in FIG. 1B that in the present embodiment, in a side projection plan viewing from the tip section 101 along the wall-attaching adjustment wire 6, the corrugated electrode frame is in a crossing mode, and the multiple electrodes 2 are arranged at the crest positions respectively. Thus, the multiple electrodes 2 are evenly distributed along the contour circumferential surface 200 (shown in dotted-lines). Of course, when the crossing angles of the corrugations are configured to be different, the multiple electrodes 2 can be distributed unevenly in the side projection plan.

Each of the intermediate section 103 extends along the diameter of the contour circumferential surface 200 (as shown in FIG. 1B), or extends along one side of an inner joint triangle of contour circumferential surface 200 (as shown in FIG. 10B). Such a configuration enables each intermediate section 103 suffer forces from the electrodes 2 fixed at both ends of the intermediate section 103. Thus, each intermediate section 103 presses firmly to the wall of the blood vessel under combined forces from the electrodes at both ends.

Figure 2:
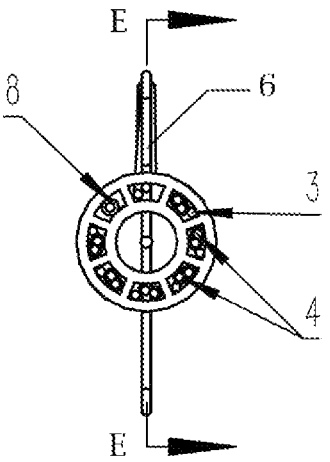
FIG. 2 is a cross section view of an electrode frame of the corrugated radiofrequency ablation catheter shown in FIG. 1A.
Figure 3A:
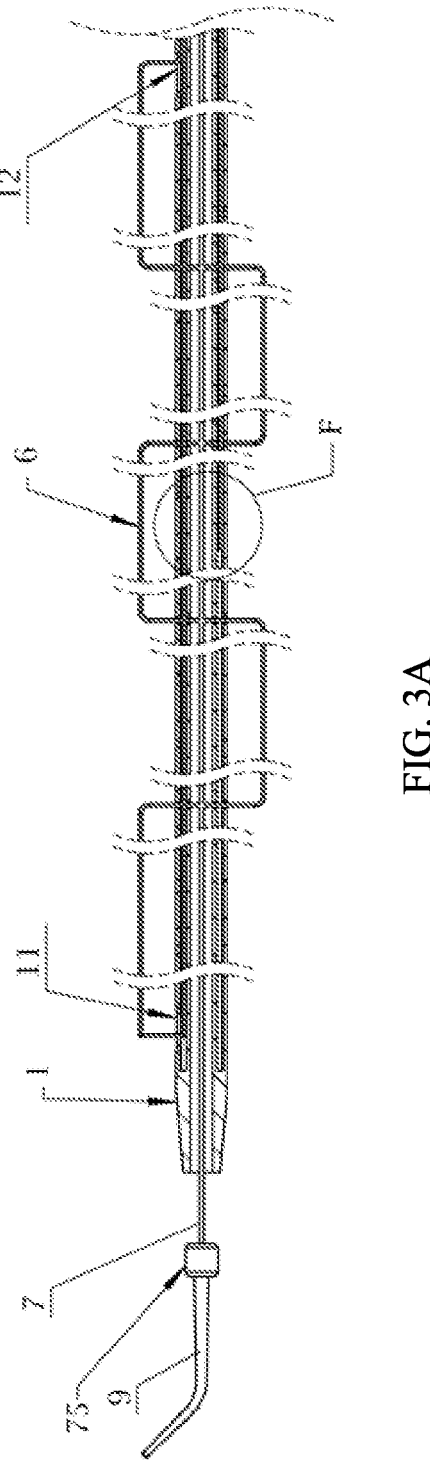
FIG. 3A is an E-E section view of the electrode frame shown in FIG. 2.
Figure 3B:
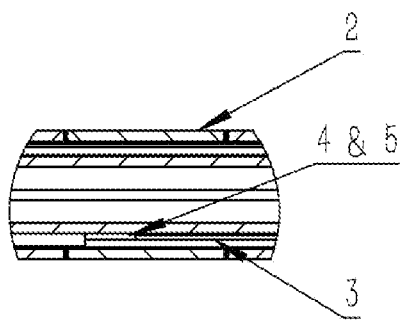
FIG. 3B is an enlarged view of an F portion shown in FIG. 3A.

It can be learned from internal section views as shown in FIG. 2, FIG. 3A and FIG. 3B that the outer tube 1 of the electrode frame can be a single-lumen tube or a multi-lumen tube, and the outer tube 1 can be made of a polymer material or a metal material, such as stainless steel or memory alloy. The outer tube 1 can be machined from a straight tube, and then preformed into a corrugated tube. As shown in FIG. 2, when the outer tube 1 is a multi-lumen tube, multiple lumens are provided inside the outer tube 1 of the electrode frame besides a central lumen, and a set of radiofrequency cables 3 and thermocouple wires 4 is arranged in the lumens. The heads of each set of radiofrequency cables 3 and thermocouple wires 4 are fixed in the tip section 101 or a single electrode 2. The heads of the radiofrequency cables 3 are tightly fixed to one electrode 2 through welding, conductive adhesive gluing or other means. The heads of the two thermocouple wires 4 are welded and coated with thermocouple wire insulating layers 5 to be insulated from the radiofrequency cables 3 and the electrode 2.

As shown in FIG. 2, a shaping wire 8 is further arranged in one lumen of the outer tube 1, and the shaping wire 8 is fixed in a deformation section of the electrode frame to be used for supporting the corrugated shape of the electrode frame. Of course, the electrode frame can also be directly shaped into a corrugated shape, so that the shaping wire 8 can be omitted, for example, when the outer tube is made of memory alloy or a polymer material, the outer tube can be directly shaped, so that the shaping wire 8 can be omitted.

As shown in FIG. 3, a supporting wire 7 is arranged in the central lumen inside the connecting catheter and the electrode frame, the supporting wire 7 can be movably arranged in the central lumen and can also be fixedly arranged in the central lumen, or the supporting wire 7 can be movably or fixedly arranged in other lumens of the connecting catheter and the electrode frame. A developing head 75 can be arranged at the head end of the supporting wire 7 to be used for real-time imaging of the interior of a target lumen. Meanwhile, a soft guide wire 9 can also be arranged at the front end of the supporting wire 7, the soft guide wire 9 can be a straight-head soft guide wire, and can also be a bent-head soft guide wire as shown in the figure, in this way, the radiofrequency ablation catheter can directly enter blood vessels without a guide catheter/sheath, and surgical procedures are simplified.

Figure 4:
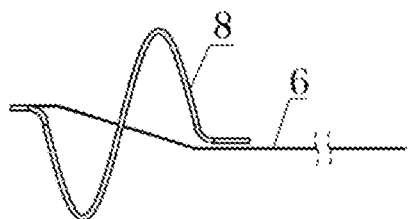
FIG. 4 is a view of another arrangement mode of a wall-attaching adjustment wire in the first embodiment.
Figure 5:
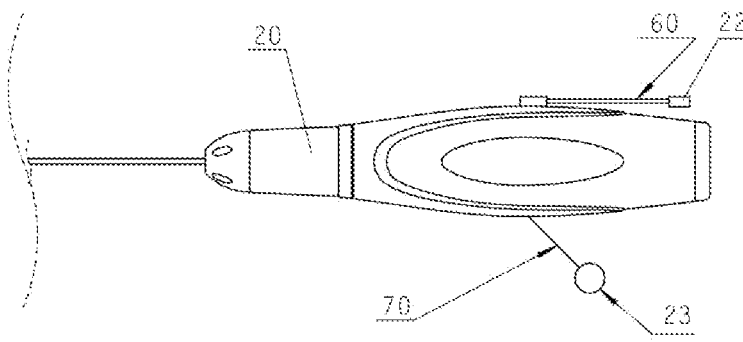
FIG. 5 is a structure diagram of a control handle of the corrugated radiofrequency ablation catheter shown in FIG. 1A in the first embodiment.

It can be learned from FIG. 2 to FIG. 5 that a lumen used for accommodating the wall-attaching adjustment wire 6 is further provided in the outer tube and the connecting catheter, and the rear section of the wall-attaching adjustment wire 6 is slidably provided within one lumen of the connecting catheter 300 and is connected at the rear end 60 onto a control element 22 provided on the control handle 20 (see FIG. 5). The wall-attaching adjustment wire 6 can slide back and forth in the lumen of the connecting catheter 300 and the outer tube 1. The lumen for accommodating the wall-attaching adjustment wire 6 can be the central lumen or one of the lumen rounding the central lumen. As shown in FIG. 1A, the front section of the wall-attaching adjustment wire 6 runs through a hole 12 near the rear end of the electrode frame and multiple holes provided on different corrugations, and finally the front end of the wall-attaching adjustment wire 6 runs through a hole 11 near the front end of the electrode frame and returns to the interior of the electrode frame to be fixed. The wall-attaching adjustment wire 6 can slide in the holes provided on different corrugations.

The front end of the wall-attaching adjustment wire 6 can be fixed at different positions, and the front end of the wall-attaching adjustment wire 6 can be fixed to the front end of the electrode frame, to the front end of the supporting wire 7, or to the shaping wire 8, or the front end of the wall-attaching adjustment wire 6 runs through corresponding lumens in the electrode frame 2 and the connecting catheter to be fixed to the control element 22 or a housing of the control handle 20 together with the rear end 60 of the wall-attaching adjustment wire 6.

As shown in FIG. 3, each intermediate section 103 has a through-hole 1030 located at middle of the intermediate section 103 (i.e., at D/2 of the length of the intermediate section 103). All of the through-holes 1030 are co-planar. That is, they are located in a plane that contains the centerline of the outer tube 1. The through-holes 1030 allow the wall-attaching adjustment wire 6 to extend into the intermediate section 103 or extend outwardly from the intermediate section 103. In other words, the wall-attaching adjustment wire 6 penetrate the intermediate section 103 at pitch of L ($D<L<2D$).

Specifically, as shown in FIG. 3, after running through the hole 11 near the front end of the electrode frame and returning to the interior of the electrode frame 2, the front end of the wall-attaching adjustment wire 6 runs through the lumens in the electrode frame and the connecting catheter and returns to the rear end of the connecting catheter together with the rear end of the wall-attaching adjustment wire 6, and is fixed to the housing of the control handle 20 or the control element 22. In other words, the front end and the rear end of the wall-attaching adjustment wire 6 can be fixed to the same control element 22 as shown in FIG. 5, or either the front end or the rear end of the wall-attaching adjustment wire 6 is fixed to the housing of the control handle 20, and the other one is fixed to the control element 22. By pulling the control element 22, the wall-attaching adjustment wire 6 is driven to move backwards, and the diameter of the electrode frame can be changed.

Of course, the front end of the wall-attaching adjustment wire 6 can also be simply fixed to the front end of the electrode frame, or fixed to the front end of the supporting wire 7 or a certain portion, located in the electrode frame, of the supporting wire 7, or fixed to a certain position on the shaping wire 8, or the front end of the wall-attaching adjustment wire 6 is fixed in the lumen of the electrode frame, as long as the front end of the wall-attaching adjustment wire 6 is fixed, in this way, when the wall-attaching adjustment wire 6 is pulled back, contraction distortion of the electrode frame can be caused under the action of the wall-attaching adjustment wire 6, the diameters of the corrugations of the electrode frame are increased, and the axial distance between the multiple corrugations becomes smaller.

When the front end of the wall-attaching adjustment wire 6 is fixed to the supporting wire 7 or the shaping wire 8, the wall-attaching adjustment wire 6 and the supporting wire 7/shaping wire 8 can be made of the same material, and in this case, the wall-attaching adjustment wire 6 can be interpreted as a filament obtained through backward branching of the supporting wire 7/shaping wire 8.

For example, as shown in FIG. 4, the front end of the wall-attaching adjustment wire 6 and the front end of the shaping wire 8 are fixed together, in this case, the shaping wire 8 and the wall-attaching adjustment wire 6 can be made of the same kind of filament, the wall-attaching adjustment wire 6 and the shaping wire 8 are two filament branches obtained through backward branching of the front end of the filament respectively, wherein the branch corresponding to the shaping wire 8 is fixed in a certain lumen of the electrode frame, and the rear section of the branch corresponding to the wall-attaching adjustment wire 6 can slide in the lumen of the electrode frame and/or a body of the catheter. When the wall-attaching adjustment wire 6 and the shaping wire 8 are made of different materials (for example, the shaping wire 8 is made of tubing and the wall-attaching adjustment wire 6 is made of a filament), the front end/front section of the wall-attaching adjustment wire 6 and the shaping wire 8 can be assembled together through welding, riveting, bonding or other techniques.

Besides, it can be seen from FIG. 5 that in the above-mentioned structure, a control element 23 is further arranged outside the control handle 20, and the tail end 70 of the supporting wire 7 also enters the control handle 20 after protruding to the outside of the connecting catheter, and is fixed to the externally arranged control element 23 after passing through the control handle 20. Of course, the control element 22 connected with the wall-attaching adjustment wire 6 can also be provided outside the control handle 20 in an externally arranged way, and the front end and/or the rear end of the wall-attaching adjustment wire 6 passes through the control handle 20 and then is connected to the externally arranged control element 22. Similarly, the control element 23 can also be arranged on the control handle 20, and the supporting wire 7 penetrates into the control handle 20 and is then directly connected with the control element 23. When the supporting wire 7 is fixedly arranged in the connecting catheter and the electrode frame, the control element 23 used for controlling the supporting wire 7 can be omitted.

Figure 6A:
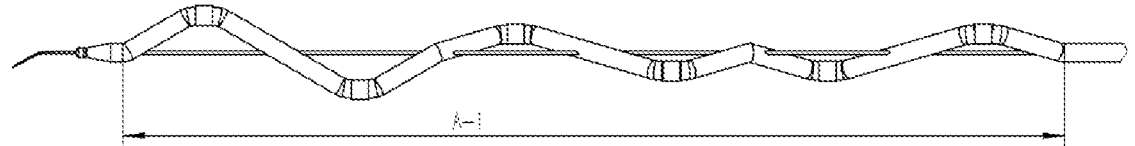
FIG. 6A is a use state view of the corrugated radiofrequency ablation catheter entering a target lumen with a small diameter in the first embodiment.
Figure 6B:
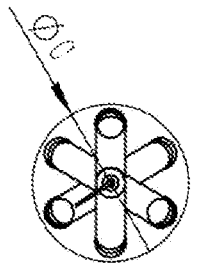
FIG. 6B is a side view corresponding to FIG. 6A.
Figure 7A:
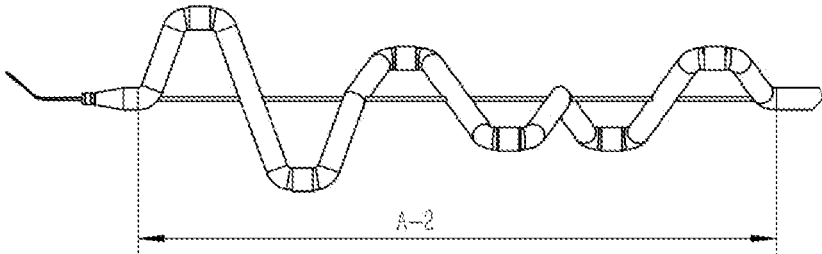
FIG. 7A is a use state view of the corrugated radiofrequency ablation catheter entering a target lumen with a large diameter in the first embodiment.

FIG. 6A to FIG. 7B show the use state views of the corrugated radiofrequency ablation catheter entering target lumens with different diameters. Suppose the corrugated electrode frame as shown in FIG. 1A has an initial diameter of $\Phi B$ ($B \leq D$) and a corrugation section length of A ($A<L$). By loosening the wall-attaching adjustment wire 6, the wall-attaching adjustment wire 6 becomes loose, at the moment, the length of a corrugation section at the front end of the catheter can be increased by means of a sheath, so that the corrugation section is approximately straight and can enter a target lumen. As shown in FIG. 6A, when the corrugated electrode frame enters a thin blood vessel through the sheath (suppose that the diameter of the target lumen $\Phi C$ is smaller than the initial diameter of the corrugations $\Phi B$), the corrugations of the electrode frame automatically expand to have a diameter close to the diameter of the target lumen $\Phi C$ (see FIG. 6B), the multiple electrodes 2 make contact with the wall of the catheter under the natural expansion of the electrode frame, at the moment, the length of the corrugation section of the electrode frame is increased to be (A-1), and the wall-attaching state of the electrodes 2 can be improved by tensioning the wall-attaching adjustment wire 6. As shown in FIG. 7A, when the corrugated electrode frame runs through the sheath and enters a thick blood vessel (suppose that the diameter of the target lumen is larger than or equal to the initial diameter of the corrugations ΦB), the electrodes 2 can not be well attached to the wall after the electrode frame expands. By pulling back the wall-attaching adjustment wire 6, the diameters of the corrugations of the electrode frame can be increased to be equal to or slightly larger than the diameter of the target lumen ΦD (see FIG. 7B), and the multiple electrodes 2 make close contact with the wall of the catheter under the action of the wall-attaching adjustment wire 6. At the moment, the length of the corrugation section of the electrode frame is shortened to be (A-2), and the axial distance between the multiple electrodes distributed on the electrode frame becomes smaller. After radiofrequency ends, by loosening the wall-attaching adjustment wire 6, the electrode frame becomes loose, then the electrode frame is made to enter the sheath by moving the sheath forward or moving the catheter backward, so that the radiofrequency ablation catheter can be rotated or moved in the target lumen, or moved out of the target lumen.

Second to Fifth Embodiments

In the second embodiment as shown in FIG. 8A and FIG. 8B, the corrugated electrode frame is composed of multiple triangular waves, and the multiple corrugations are located in the same plane. The multiple electrodes are located at the crests and troughs of the triangular waves respectively, and due to the fact that the side projection plan of the multiple triangular waves overlap, the side projection plan of the multiple electrodes overlap too. After ablation is finished once, the catheter can be rotated by a certain angle to conduct ablation on the same position of the target lumen again.

In the third embodiment as shown in FIG. 9A and FIG. 9B, the corrugated electrode frame is composed of multiple arc waves, but the multiple corrugations are located in different planes. The multiple electrodes are located at the crests (also called troughs) of the arc waves respectively, so that the side projection plan of the multiple electrodes can be distributed in the circumferential direction of the target lumen. At the moment, after ablation is finished once, the catheter can be directly moved to conduct ablation on other positions of the target lumen, and the operation of rotating the catheter at the same position of the target lumen is omitted.

In the second embodiment and the third embodiment, after running through the hole near the rear end of the electrode frame, the front section of the wall-attaching adjustment wire 6 runs through the holes provided on different corrugations, and finally the front end of the wall-attaching adjustment wire 6 runs through the hole near the front end of the electrode frame and returns to the interior of the electrode frame to be fixed.

Due to the fact that in the third embodiment, the multiple arc waves are located in different planes and the side projection plan of the multiple electrodes are distributed in the circumferential direction of the target lumen, compared with the second embodiment, the requirement of radiofrequency ablation surgery for the arrangement direction of the electrode frame in the target lumen is low in the third embodiment, and therefore operation is easy. However, the structure of the second embodiment can enter the target lumen more easily than the structure of the third embodiment.

In the fourth embodiment as shown in FIG. 10A and FIG. 10B, the multiple corrugations of the corrugated electrode frame are all located in different planes, moreover, the multiple corrugations are distributed into an approximate spiral shape, the multiple electrodes are located at the crests (also called troughs) of the corrugations respectively, and therefore the multiple electrodes can be distributed in the circumferential direction of the target lumen. In the present embodiment, the multiple corrugations can be distributed into one or more circles of spirals, and moreover, the wall-attached adjustment wire 6 can also run through the holes provided on the different corrugations.

In the fifth embodiment as shown in FIG. 11, the corrugated electrode frame is composed of multiple sine waves. Like the second embodiment, the multiple corrugations in the fifth embodiment are located in the same plane, and moreover, the multiple electrodes are located at the crests and troughs of the sine waves respectively. But different from the second embodiment, the front section of the wall-attached adjustment wire 6 is fixed at the front end after running around the multiple corrugations instead of running through the multiple corrugations.

It can be learned from the above five embodiments that the multiple corrugations in the corrugated electrode frame can be in the shape of a triangular wave (see FIG. 8A) composed of several straight line segments, an arc wave (see FIG. 10A) or sine wave (see FIG. 11) composed of several arc segments, a trapezoidal wave composed of straight lines and curves, or any other corrugations not shown in the figures. The multiple corrugations can be distributed in the same plane, can also be distributed in different planes, and can even be distributed into an approximate spiral shape in an encircling mode, so that the electrodes can be distributed in the circumferential direction. Compared with the situation that the multiple corrugations are distributed in the same plane, when the multiple corrugations are distributed in different planes, the corrugated electrode frame can be attached to the wall in any direction in the target lumen during actual ablation surgery. In the above-mentioned embodiments as shown in the figures, on the same electrode frame, the multiple corrugations forming the corrugated shape are in the same shape. Of course, the multiple corrugations forming the corrugated shape can have different shapes and sizes, and the corrugations can be different in form, spacing, crest position, trough position and the like. When the corrugated electrode frame consists of corrugations in different sizes, the wall-attaching states of local electrodes can be adjusted by adjusting the sizes of the corrugations in a local area, and at the same time when the wall-attaching states are adjusted, and meanwhile, the forms of other areas may not be adjusted. Wall-attaching adjustment of the corrugated electrode frame consisting of different corrugations can be achieved by pulling different filament branches in the wall-adjustment adjustment wire 6 composed of multiple filaments. Please see the ninth embodiment for the structure of the wall-adjustment adjustment wire 6 composed of multiple filaments and the wall-attaching adjustment way.

Besides, in the radiofrequency ablation catheter, the wall-adjustment adjustment wire 6 can be arranged in multiple ways, the front section of the wall-adjustment adjustment wire 6 can run through the holes in the outer tube provided with the multiple corrugations as in the first, second and third embodiments, and can also directly run around the corrugations and then enter the electrode frame to be fixed instead of passing through the outer tube with the multiple corrugations. Compared with the arrangement mode that the front section of the wall-adjustment adjustment wire 6 is entirely exposed from the electrode frame, by allowing the wall-adjustment adjustment wire 6 to run through the holes in different corrugations of the outer tube, the shape change of the electrode frame is controllable, and the wall-attaching effect is better.

Fifth Embodiment

Only the form of the electrode frame and the arrangement mode of the front section of the wall-adjustment adjustment wire 6 are briefly introduced above, now detailed explanation will be given on the specific structure of the wall-adjustment adjustment wire 6 in the radiofrequency ablation catheter and the structure of the corresponding control handle 20 with reference to FIG. 11 to FIG. 15B and the fifth embodiment.

According to the radiofrequency ablation catheter as shown in FIG. 11, the structure of the wall-adjustment adjustment wire 6 inside the radiofrequency ablation catheter can be similar to the structure in the first embodiment, that is to say, the wall-adjustment adjustment wire 6 is a monofilament independent of the supporting wire 7 and the shaping wire 8; the wall-adjustment adjustment wire 6 also has the function of the supporting wire, or the front end of the wall-adjustment adjustment wire 6 can be fixed to the supporting wire 7 to serve as a branch of the supporting wire 7. Both the supporting wire 7 and the wall-adjustment adjustment wire 6 can be made of a filament or a thin tube.

Figure 13:
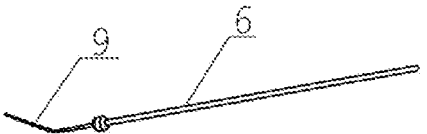
FIG. 13 is a second exemplary structure of the wall-attaching adjustment wire in the corrugated radiofrequency ablation catheter shown in FIG. 11.

As shown in FIG. 12 and FIG. 13, when the wall-adjustment adjustment wire 6 has the function of the supporting wire, the rear section of the wall-adjustment adjustment wire 6 is slidably provided within a certain lumen of the connecting catheter and connected at the rear end onto the control handle 20; and after the front section of the wall-attaching adjustment wire 6 runs around the multiple corrugations or runs through the holes provided on the different corrugations, the front end of the wall-attaching adjustment wire 6 runs through the hole 11 near the front end of the electrode frame, returns to the interior of the electrode frame, protrudes out of the front end of the electrode frame and is fixed to the front end of the electrode frame or limited outside the front end of the electrode frame. A developing head and/or soft guide wire 9 can be provided at the front end of the wall-attaching adjustment wire 6. The soft guide wire 9 can be a straight-head soft guide wire as shown in FIG. 12, and can also be a bent-head soft guide wire as shown in FIG. 13. The bent-head soft guide wire can be composed of multiple arcs, straight lines or curves, and can have one or more elbows. When the soft guide wire is provided at the front end of the wall-attaching adjustment wire 6, the radiofrequency ablation catheter can enter a blood vessel and reach a required position under the guidance of a sheathless pipe.

Figure 14:
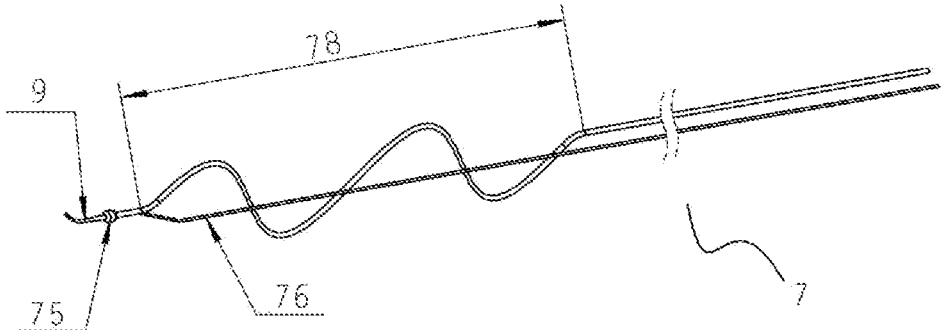
FIG. 14 is a third exemplary structure of the wall-attaching adjustment wire in the corrugated radiofrequency ablation catheter shown in FIG. 11.

As shown in FIG. 14, when the front end of the wall-attaching adjustment wire 6 is fixed to the supporting wire 7, the wall-attaching adjustment wire 6 can be seen as a backward branch 76 of the supporting wire 7. In this case, one or two lumens exist inside the connecting catheter and the electrode frame to be used for accommodating two branches of the supporting wire 7. When no shaping wire 8 is independently arranged inside the electrode frame, the portion, corresponding to the electrode frame, of the front part of the supporting wire 7 can be configured to be a corrugation shaping section 78 through pre-shaping, the branch, corresponding to the corrugation shaping section 78, of the supporting wire 7 is fixed to the interior of the corresponding lumen, and the rear end can be directly fixed in the connecting catheter and can also be fixed in the control handle, so that the electrode frame can remain in a corrugated shape when no external force is applied; the branch 76, corresponding to the wall-attaching adjustment wire, of the supporting wire 7 can be slidably arranged in the lumen, and the tail end can be fixed to the control element provided on the control handle 20 or to the control element arranged externally. When the supporting wire 7 does not have the function of the shaping wire 8, the supporting wire 7 and the wall-attaching adjustment wire 6 can be slidably arranged in the same lumen or in two different lumens, the rear extremities of the supporting wire 7 and the wall-attaching adjustment wire 6 are fixed to the corresponding control element provided on the control handle 20 or to the corresponding control element arranged externally after protruding to the outside of the connecting catheter.

Figure 15A:
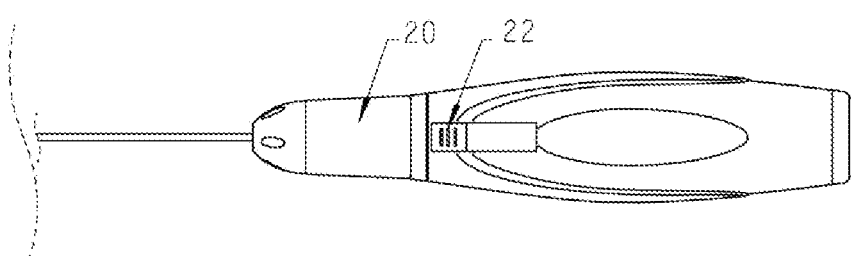
FIG. 15A is a first use state view of a control handle of the corrugated radiofrequency ablation catheter in the fifth embodiment.
Figure 15B:
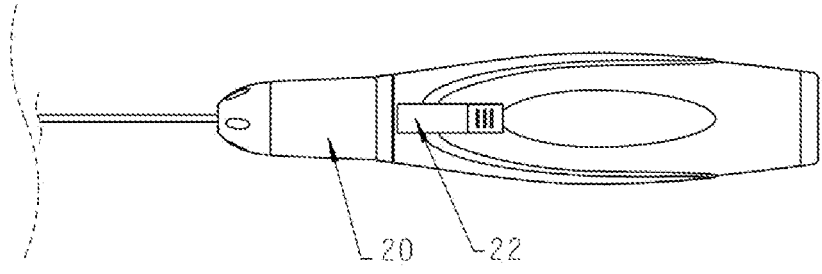
FIG. 15B is a second use state view of the control handle of the corrugated radiofrequency ablation catheter in the fifth embodiment.

When the wall-attaching adjustment wire 6 is combined with the supporting wire 7, or the supporting wire 7 has the function of the shaping wire 8, there can be only one control element 22 connected with the wall-attaching adjustment wire 6 on the control handle 20. Please see FIG. 15A and FIG. 15B for the structure of the control handle 20 in this case. By pushing the control element 22 back to the position as shown in FIG. 15B from the position as shown in FIG. 15A, the wall-attaching adjustment wire 6 can be pulled back, so that the diameter of the electrode frame is increased.

Sixth Embodiment

Figure 16:
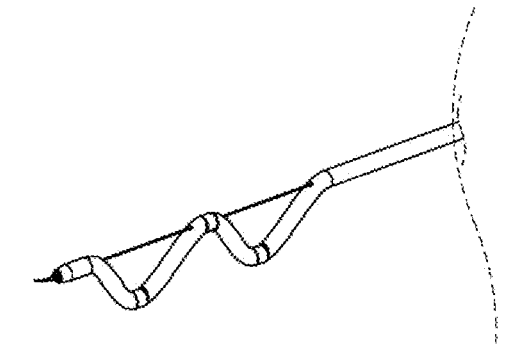
FIG. 16 is a three-dimensional structure diagram of a corrugated radiofrequency ablation catheter in a sixth embodiment.
Figure 17:
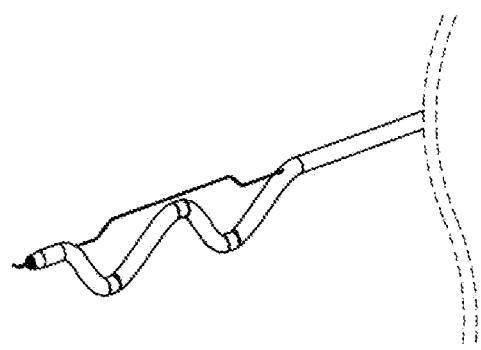
FIG. 17 is a three-dimensional structure diagram of a second corrugated radiofrequency ablation catheter in the sixth embodiment.

FIG. 16 and FIG. 17 are two structure diagrams of the radiofrequency ablation catheter in the sixth embodiment.

From the first embodiment to the fifth embodiment, whether the multiple corrugations are distributed in the same plane or in different planes, and whether the wall-attaching adjustment wire 6 runs through the holes provided on the corrugations, the wall-attaching adjustment wire 6 is arranged near the center of the electrode frame. The sixth embodiment is different from all the five embodiments mentioned above in that the wall-attaching adjustment wire 6 in the present embodiment is eccentrically arranged on the corrugated electrode frame, and the wall-attaching adjustment wire 6 can be located at the highest point of the electrode frame and can also be located at any position between the center and the vertex of the electrode frame.

In the structure as shown in FIG. 16, the wall-attaching adjustment wire 6 is eccentrically arranged on the corrugated electrode frame, and the front section of the wall-attaching adjustment wire 6 penetrates out of the hole near the rear end of the electrode frame, runs through the holes provided on the corrugations, then runs through the hole near the front end of the electrode frame and enters the front end of the electrode frame to be fixed.

In the structure as shown in FIG. 17, the wall-attaching adjustment wire 6 is eccentrically arranged on the corrugated electrode frame, and the front section of the wall-attaching adjustment wire 6 penetrates out of the hole near the rear end of the electrode frame, runs around the multiple corrugations, runs through the hole near the front end of the electrode frame and then enters the front end of the electrode frame to be fixed.

When the front end of the wall-attaching adjustment wire 6 runs around the multiple corrugations, the diameter of the contracted corrugated shape can be greatly increased by pulling the wall-attaching adjustment wire 6, and ideally, the electrode frame can be adapted to blood vessels with diameters larger than the diameter of the corrugation section of the electrode frame. Due to the fact that the range of the diameters of human blood vessels is fixed, the initial diameter of the corrugation shape of the electrode frame in the radiofrequency ablation catheter can be reduced substantially, so that the radiofrequency ablation catheter can enter blood vessels and move in blood vessels easily.

Seventh Embodiment

Figure 18:
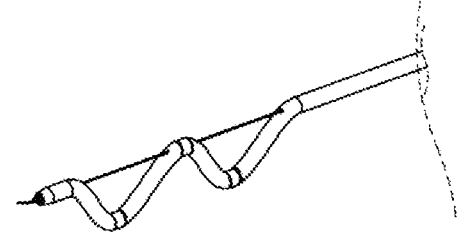
FIG. 18 is a three-dimensional structure diagram of a corrugated radiofrequency ablation catheter in a seventh embodiment.

In the radiofrequency ablation catheter as shown in FIG. 18, the electrode frame has two corrugations, the wall-attaching adjustment wire 6 is eccentrically arranged, and the wall-attaching adjustment wire 6 can be composed of one filament or two filaments.

Figure 19:
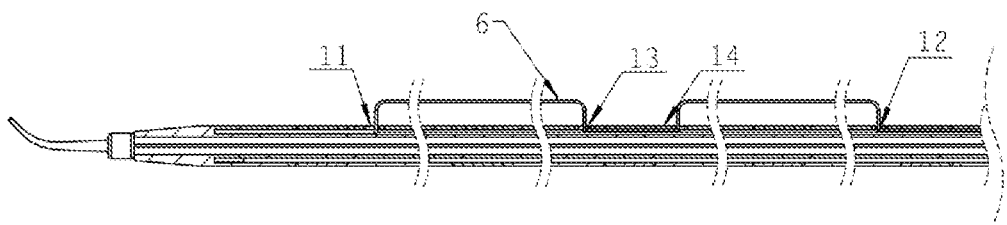
FIG. 19 is a first exemplary structure of a wall-attaching adjustment wire in the corrugated radiofrequency ablation catheter shown in FIG. 18.

In the structure as shown in FIG. 19, the wall-attaching adjustment wire 6 is composed of one filament, the rear section of the wall-attaching adjustment wire 6 runs through the lumen in the connecting catheter and returns to the interior of the control handle, and the rear end of the wall-attaching adjustment wire 6 is fixed to the control element provided on the control handle or the control element arranged externally; the middle section of the wall-attaching adjustment wire 6 penetrates out of the hole 12 near the rear end of the electrode frame, and then two points are fixed to the interior of a hole 13 and a hole 14 provided at the crest at the middle position between two corrugations respectively; then the front end of the wall-attaching adjustment wire 6 runs through the hole 11 near the front end of the electrode frame, enters the interior of the electrode frame, runs through the lumens in the electrode frame and the connecting catheter, returns to the rear end of the connecting catheter, and is fixed to the same control element or to different control elements respectively with the rear end. In such a structure, both the front section and the rear section of the wall-attaching adjustment wire 6 run through the lumen inside the connecting catheter, the front end and the rear end of the wall-attaching adjustment wire 6 are fixed to the corresponding control elements respectively, and both of the two corresponding control elements can be arranged on the control handle 20 or outside the control handle 20, or one control element is arranged on the control handle 20, and the other control element is arranged outside the control handle 20. The front section and the rear section of the wall-attaching adjustment wire 6 are controlled through the two corresponding control elements respectively, and the contraction degrees of two corrugations can be separately adjusted. Furthermore, the front end and the rear end of the wall-attaching adjustment wire 6 can be fixed to the same control element.

Figure 20:
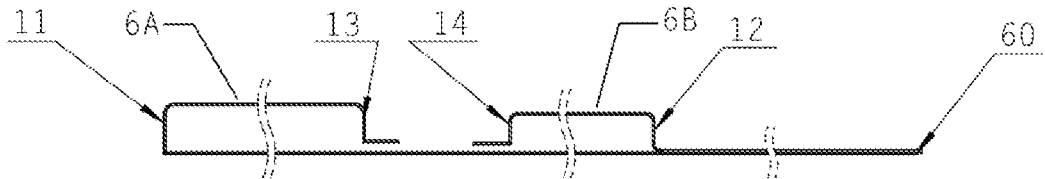
FIG. 20 is a second exemplary structure of the wall-attaching adjustment wire in the corrugated radiofrequency ablation catheter shown in FIG. 18.
Figure 21:
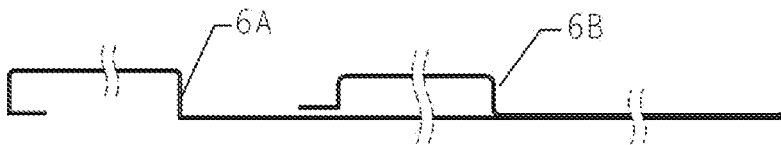
FIG. 21 is a third exemplary structure of the wall-attaching adjustment wire in the corrugated radiofrequency ablation catheter shown in FIG. 18.

As shown in FIG. 20 and FIG. 21, in the structure as shown in FIG. 18, the wall-attaching adjustment wire 6 can also be composed of two filaments 6A and 6B used for adjusting two corrugations respectively, the front end of each filament is fixed to one end of the corresponding corrugation, and the other end of each filament runs around the corresponding corrugation, returns to the interior of the electrode frame from the other end of the corrugation, runs through the lumens in the electrode frame and the connecting catheter, returns to the control handle, and is then fixed to the corresponding control element arranged on the control handle or arranged externally.

In FIG. 20, the front end of the filament 6A is fixed in the hole 13 provided between the two corrugations, and the rear end of the filament 6A runs through the hole 11 near the front end of the electrode frame, returns to the interior of the electrode frame, runs through the lumens in the electrode frame and the connecting catheter, returns to the control handle, and is then fixed to the corresponding control element; the front end of the filament 6B is fixed in the other hole 14 provided between the two corrugations, and the rear end of the filament 6B runs through the hole 12 near the rear end of the electrode frame, returns to the interior of the electrode frame, runs through the lumens in the electrode frame and the connecting catheter, returns to the control handle, and is then fixed to the corresponding control element. In FIG. 21, the filament 6B is arranged in the same way as FIG. 20, the front end of the filament 6A is fixed in the hole 11 near the front end of the electrode frame, and the rear end of the filament 6A runs through the hole 13 provided between the two corrugations, returns to the interior of the electrode frame, runs through the lumens in the electrode frame and the connecting catheter, and is then fixed to the corresponding control element. The two corresponding control elements fixed to the filament 6A and the filament 6B respectively can be arranged on the control handle 20 or outside the control handle 20. The wall-attaching adjustment wire parts 6A and 6B are used for controlling the contraction degrees of the two corrugations respectively. The wall-attaching adjustment wire parts 6A and 6B are controlled through the two corresponding control elements respectively, and the contraction degrees of two corrugations can be separately adjusted. Furthermore, the corresponding control elements of the filament 6A and the filament 6B can be the same control element.

Eighth Embodiment

Figure 22:
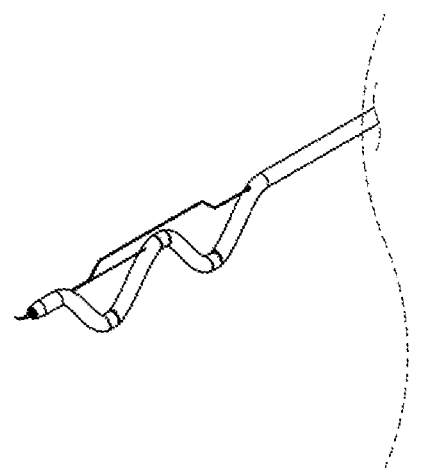
FIG. 22 is a three-dimensional structure diagram of a corrugated radiofrequency ablation catheter in an eighth embodiment.
Figure 23:
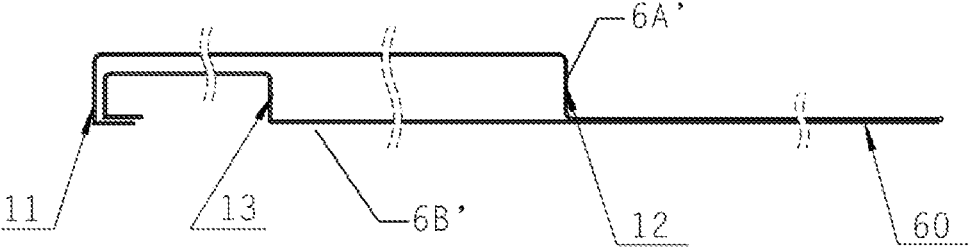
FIG. 23 is a structure diagram of a wall-attaching adjustment wire in the corrugated radiofrequency ablation catheter shown in FIG. 22.

In the eighth embodiment as shown in FIG. 22 and FIG. 23, the wall-attaching adjustment wire 6 is composed of two filaments 6A' and 6B' used for adjusting one corrugation and one section of corrugations (namely a corrugation section) respectively, the front end of each filament is fixed to one end of the corresponding corrugation/corrugation section, and the other end of each filament runs around the corresponding corrugation/corrugation section, returns to the interior of the electrode frame from the other end of the corrugation/corrugation section, runs through the lumens in the electrode frame and the connecting catheter, returns to the control handle, and is fixed to the corresponding control elements. As shown in FIG. 23, the front end of the filament 6A' and the front end of the filament 6B' are both fixed in the hole 11 near the front end of the electrode frame, and the rear extremities 60 of the two filaments run through the hole 13 provided between two corrugations and the hole 12 near the rear end of the electrode frame respectively, return to the interior of the electrode frame, and are finally fixed to the corresponding control elements. The filament 6A' is used for controlling the contraction degree of the single corrugation near the front end of the electrode frame, the filament 6B' is used for controlling the whole corrugation section, in the present embodiment as shown in the figure, the whole corrugation section comprises two corrugations, that is to say, the filament 6B' is used for controlling the contraction degree of two corrugations. The corrugation section adjusted by the filament 6B' comprises the single corrugation adjusted by the filament 6A'. In the present embodiment, the corresponding control elements connected with the rear extremities of the two filaments respectively can also be one control element.

It can be learned from the seventh embodiment and the eighth embodiment that when the electrode frame has two or more corrugations, the wall-attaching adjustment wire 6 can be composed of two or more filaments, the multiple filaments are used for adjusting one corrugation or one section of corrugations on the electrode frame respectively, wherein one section of corrugations comprises two or more corrugations, the front end of each filament is fixed to one end of the corresponding corrugation/corrugation section, and the other end of each filament runs around the corrugation/ corrugation section, returns to the interior of the electrode frame from the other end of the corrugation/corrugation section, runs through the lumens in the electrode frame and the connecting catheter and is fixed to the corresponding control elements. When one filament is used for adjusting a single corrugation, the front end of the filament is fixed to one end of the corrugation, and the rear end of the filament runs through the hole formed in the other end of the corrugation and penetrates into the electrode frame; when one filament is used for adjusting a certain section of corrugations, the front end of the filament is fixed to one end of the section of corrugations, and the rear end of the filament runs through the hole formed in the other end of the section of corrugations and penetrates into the electrode frame. The multiple sections of corrugations controlled by the multiple filaments respectively can overlap. In the structure shown in FIG. 20 and FIG. 21, the wall-attaching adjustment wire has two filaments, and the two filaments are used for adjusting two corrugations on the electrode frame respectively; while in the structure of the eighth embodiment shown in FIG. 22 and FIG. 23, the wall-attaching adjustment wire 6 has two filaments, and the two filaments are used for controlling one corrugation and one section of corrugations on the electrode frame respectively.

When multiple control elements are adopted to control different corrugation sections of the electrode frame, after the radiofrequency ablation catheter enters a target position, the corresponding corrugation sections of the electrode frame can be expanded in a segmented mode as needed, in other words, only the diameters of the corrugation sections requiring radiofrequency are changed, in this way, the diameters of different corrugation sections of the electrode frame can be adjusted more flexibly, and the wall-attaching adjustment difficulty of the radiofrequency ablation catheter is reduced.

Furthermore, the rear extremities of the multiple filaments can also be fixed to one control element, so that one control element can control all the filaments.

Ninth Embodiment

Figure 24:
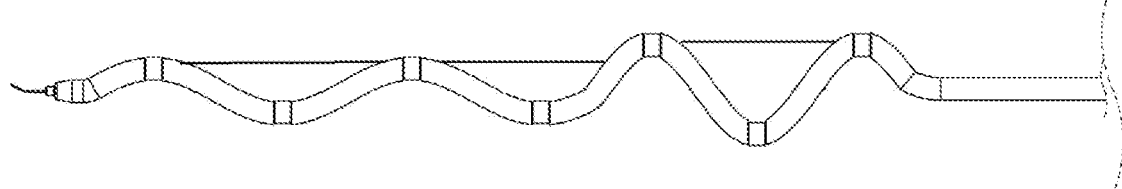
FIG. 24 is a three-dimensional structure diagram of a corrugated radiofrequency ablation catheter in a ninth embodiment.

As shown in FIG. 24, the electrode frame of the radiofrequency ablation catheter provided in the present embodiment is composed of multiple corrugations in different sizes. Every corrugation can have its own size, or part of the corrugations can have one size and others have a different size. Besides, the multiple corrugations are provided from the front end to the rear end of the electrode frame in a size increasing mode, or the multiple corrugations are provided from the front end to the rear end of the electrode frame in a size reducing mode. In this case, the wall-attaching adjustment wire 6 composed of multiple filaments is arranged in the radiofrequency ablation catheter, the different filaments are used for controlling different parts of the electrode frame respectively, and the corrugation size of a corresponding area of a corrugation section can be changed by pulling different filaments, so that local wall attaching of the electrode frame can be achieved. Please refer to the sixth embodiment and the seventh embodiment for the specific arrangement mode of the wall-attaching adjustment wire 6 composed of multiple filaments, and the descriptions thereof are omitted herein.

When the multiple corrugations are provided from the front end to the rear end of the electrode frame in a size increasing mode, the radiofrequency ablation catheter using the electrode frame is suitable for the situation that the diameter of a target lumen becomes smaller gradually. For example, the radiofrequency ablation catheter can enter a small branch blood vessel with a small diameter from a blood vessel with a large diameter for ablation. In this case, the multiple filaments corresponding to small-diameter corrugation sections can be controlled to allow the small-diameter corrugation sections to be well attached to the wall, so that the small branch blood vessel can be ablated by means of the small-diameter corrugation sections; or, large-diameter corrugation sections and the small-diameter corrugation sections can be attached to the wall at the same time by controlling the multiple filaments, so that the large blood vessel and the small blood vessel can be ablated at the same time or in sequence.

When the multiple corrugations are provided from the front end to the rear end of the electrode frame in a size reducing mode, the radiofrequency ablation catheter using the electrode frame is suitable for the situation that the diameter of a target lumen becomes larger gradually. For example, the radiofrequency ablation catheter is suitable for sympathetic denervation ablation of the pelvis region via the urethral system, the catheter runs through the urethra, enters the bladder, enters the fallopian tube and reaches the pelvis region, at the moment, the large-diameter corrugation sections can be well attached to the wall of the pelvis region and the small-diameter corrugation sections can be well attached to the wall of the fallopian tube by adjusting the wall-attaching adjustment wire, so that sympathetic nerves near the fallopian tube and the pelvis region can be ablated at the same time.

In conclusion, the wall-attaching adjustment wire is arranged in the corrugated radiofrequency ablation catheter, and the corrugation diameter of the electrode frame can be changed by pulling back the wall-attaching adjustment wire, so that the wall-attaching state of the electrodes can be improved, and the radiofrequency ablation catheter can be adapted to blood vessels in different diameters. Furthermore, the wall-attaching adjustment wire can be of a multi-filament structure, so as to control different corrugation sections of the radiofrequency ablation catheter, and reduce the difficulty of diameter adjustment.

In actual clinical treatment, the radiofrequency ablation catheter and a radiofrequency ablation apparatus provided by the present invention can be applied to different positions and blood vessels or tracheae with different diameters for neuroablation. For example, the radiofrequency ablation catheter and the radiofrequency ablation apparatus can be applied to neuroablation in the renal artery to treat resistant hypertension, neuroablation in the arteria coeliaca to treat diabetes, trachea/bronchus vagus nerve branch ablation to treat asthma, and duodenum vagus nerve branch ablation to treat duodenal ulcers; besides, the radiofrequency ablation catheter and the radiofrequency ablation apparatus can also be used for neuroablation in other blood vessels or tracheae like pelvis and pulmonary artery. It should be noted that the radiofrequency ablation catheter provided by the present invention is not limited to the applications listed above, but can be applied to neuroablation of other portions.

Above is the introduction of the radiofrequency ablation catheter provided by the present invention, and the present invention also provides a radiofrequency ablation apparatus comprising the radiofrequency ablation catheter. Besides the radiofrequency ablation catheter, the radiofrequency ablation apparatus also comprises a radiofrequency ablation main unit connected with the radiofrequency ablation catheter. The wall-attaching adjustment wire inside the electrode frame is correspondingly connected to the control handle after running through the connecting catheter, and the shape of the electrode frame can be changed by pulling the wall-attaching adjustment wire through the control handle, so that the electrode frame can be well attached to the wall in target lumens with different diameters. Furthermore, the radiofrequency cables and the thermocouple wires in the electrode frame are connected to corresponding circuits in the radiofrequency ablation main unit respectively through the connecting catheter, so that the radiofrequency ablation main unit can conduct radiofrequency control and temperature monitoring on the multiple electrodes. The arrangement of the control handle and the radiofrequency ablation main unit can be found in previous published patent applications of the applicant, and the descriptions of specific structures thereof are omitted herein.

In brief, since the length of the intermediate sections is L (D<L<2D), and the intermediate sections extending along the diameter of the contour circumferential surface, or extending along one side of an inner joint triangle of the contour circumferential surface, the electrodes at both ends of each intermediate section can press firmly and evenly against the wall of the blood vessel along the elongated catheter, which is adapted to ablate elongated blood vessel or the like. The multiple electrodes distributed along the elongated catheter and located at both ends of the intermediate section, provides the radiofrequency ablation at one position and then are rotated by the operator to perform the radiofrequency ablation at another position, which improves operation efficiency. The wall-attaching adjustment wire penetrates the intermediate sections at middle of the intermediate sections, thus the intermediate sections could be extended or shorten to adapt to blood vessels with different diameter while provide evenly force against the wall of the blood vessels.

Above is detailed description of the corrugated radiofrequency ablation catheter having the wall-attaching adjustment wire and the apparatus thereof provided by the present invention. For those of ordinary skill in the art, any obvious change made to the present invention without departing from the essential content of the present invention shall fall within the protection scope of the patent of the present invention.

What is claimed is:

1. A corrugated radiofrequency ablation catheter having a wall-attaching adjustment wire, provided with a connecting catheter, an electrode frame provided at the front end of the connecting catheter, and a control handle provided at the rear end of the connecting catheter; wherein the electrode frame is a corrugated electrode frame comprising multiple intermediate sections, each intermediate section having electrodes at both ends thereof; each of the intermediate sections extends along a diameter of a contour circumferential surface or extends along one side of an inner joint triangle of the contour circumferential surface; the electrodes located on the contour circumferential surface;

each of the intermediate sections has a through-hole at the middle of the respective intermediate section of the wall-attaching adjustment wire to extend into the intermediate sections or extend outwardly from the intermediate sections;

a rear section of the wall-attaching adjustment wire is slidably provided within the connecting catheter and is connected to the control handle or connected onto a control element provided outside of the control handle; a front section of the wall-attaching adjustment wire protrudes to the outside of the electrode frame and either runs through one or more holes provided on the corrugations or runs around the multiple corrugations, and then the front end returns to the interior of the electrode frame to be fixed.

2. The corrugated radiofrequency ablation catheter according to claim 1, wherein the through-hole locates at D/2 of each of the intermediate sections, wherein D is a diameter of the contour circumferential surface.

3. The corrugated radiofrequency ablation catheter according to claim 2, wherein the electrode frame further comprises a tip section and a rear section, which are of D/2 in length.

4. The corrugated radiofrequency ablation catheter according to claim 1, wherein the wall-attaching adjustment wire penetrates the intermediate sections at pitch of L, wherein D<L<2D.

5. The corrugated radiofrequency ablation catheter according to claim 4, wherein a length of each of the intermediate sections is the pitch L.

6. The corrugated radiofrequency ablation catheter according to claim 5, wherein after returning to the interior of the electrode frame, the front end of the wall-attaching adjustment wire runs through lumens in the electrode frame and the connecting catheter, returns to the rear end of the connecting catheter, and is fixed to the control handle or the control element.

7. The corrugated radiofrequency ablation catheter according to claim 5, wherein the corrugated radiofrequency ablation catheter further comprises a supporting wire provided in a certain lumen of the connecting catheter and the electrode frame.

8. The corrugated radiofrequency ablation catheter according to claim 5, wherein the corrugated radiofrequency ablation catheter further comprises a shaping wire provided within the electrode frame.

9. The corrugated radiofrequency ablation catheter according to claim 7, wherein a developing head and/or soft guide wire is provided at the front end of the supporting wire.

10. The corrugated radiofrequency ablation catheter according to claim 7, wherein a second control element used for being fixed to the tail end of the supporting wire is further provided on the control handle or outside the control handle.

11. The corrugated radiofrequency ablation catheter according to claim 5, wherein the wall-attaching adjustment wire is composed of two or more filaments, the multiple filaments are used for adjusting one corrugation or one section of corrugations on the electrode frame respectively, one section of corrugations comprises two or more corrugations, the front end of each filament is fixed to one end of the corresponding corrugation/corrugation section, and the other end of each filament runs around the corresponding corrugation/corrugation section, runs through lumens in the electrode frame and the connecting catheter, and is then fixed to the corresponding control element provided on the control handle or arranged externally.

12. The corrugated radiofrequency ablation catheter according to claim 11, wherein sections of corrugations respectively controlled by the multiple filaments overlap.

13. The corrugated radiofrequency ablation catheter according to claim 5, wherein the multiple corrugations constituting the electrode frame are provided from the front end to the rear end of the electrode frame in a size increasing mode, or the multiple corrugations constituting the electrode frame are provided from the front end to the rear end of the electrode frame in a size reducing mode.

14. A radiofrequency ablation apparatus, characterized by comprising the radiofrequency ablation catheter according to claim 1, and a radiofrequency ablation main unit connected with the radiofrequency ablation catheter.

\*   \*   \*   \*   \*